（12）United States Patent
Bomgarden et al.

(10) Patent No.: US 8,945,861 B2
(45) Date of Patent: Feb. 3, 2015

(54) METHODS FOR ISOTOPICALLY LABELING BIOMOLECULES USING MAMMALIAN CELL-FREE EXTRACTS

(75) Inventors: Ryan D. Bomgarden, Winnebago, IL (US); Eric Leigh Hommema, Roscoe, IL (US); John Charles Rogers, Rockton, IL (US); Penny JoAnn Jensen, Marengo, IL (US); Derek Karl Baerenwald, Minneapolis, MN (US)

(73) Assignee: Pierce Biotechnology, Inc., Rockford, IL (US)

( * ) Notice: Subject to any disclaimer, the term of this patent is extended or adjusted under 35 U.S.C. 154(b) by 78 days.

(21) Appl. No.: 13/565,135

(22) Filed: Aug. 2, 2012

(65) Prior Publication Data

US 2013/0034867 A1 Feb. 7, 2013

Related U.S. Application Data

(60) Provisional application No. 61/514,695, filed on Aug. 3, 2011.

(51) Int. Cl.
*C12P 21/00* (2006.01)
*G01N 33/566* (2006.01)
*G01N 25/00* (2006.01)
*G01N 33/68* (2006.01)
*C12P 21/02* (2006.01)

(52) U.S. Cl.
CPC ............ *C12P 21/02* (2013.01); *G01N 33/6848* (2013.01); *G01N 2560/00* (2013.01)
USPC ............ 435/7.92; 435/40.5; 435/7.1; 435/23; 435/68.1; 435/194

(58) Field of Classification Search
CPC combination set(s) only.
See application file for complete search history.

(56) References Cited

U.S. PATENT DOCUMENTS

| | | | |
|---|---|---|---|
| 6,391,649 | B1 | 5/2002 | Chait et al. |
| 6,762,041 | B2 | 7/2004 | Shimba et al. |
| 7,125,685 | B2 | 10/2006 | Chen |
| 7,608,248 | B2 | 10/2009 | Kainosho et al. |
| 7,759,130 | B2 | 7/2010 | Oda et al. |
| 7,939,331 | B2 | 5/2011 | Leite et al. |
| 2003/0077840 | A1 | 4/2003 | Chait et al. |
| 2007/0082399 | A1 | 4/2007 | Egorova-Zachernyuk |
| 2007/0134806 | A1 | 6/2007 | Oda et al. |
| 2008/0076905 | A1 | 3/2008 | Yokoyama et al. |
| 2009/0176199 | A1 | 7/2009 | Lee et al. |
| 2010/0173786 | A1 | 7/2010 | Brun et al. |
| 2010/0311097 | A1 | 12/2010 | Anderson |
| 2011/0022326 | A1 | 1/2011 | Oda et al. |

OTHER PUBLICATIONS

Oda Y, et al. (1999) Accurate quantitation of protein expression and site-specific phosphorylation. Proc Natl Acad Sci U S A. 96(12):6591-6.

Ong SE, et al. (2002) Stable isotope labeling by amino acids in cell culture, SILAC, as a simple and accurate approach to expression proteomics. Mol Cell Proteomics. (5):376-86.

Beynon RJ, et al. (2005) Multiplexed absolute quantification in proteomics using artificial QCAT proteins of concatenated signature peptides. Nat Methods. 2(8):587-9.

Pratt JM, et al. (2006) Multiplexed absolute quantification for proteomics using concatenated signature peptides encoded by QconCAT genes. Nat Protoc. 2006;1(2):1029-43.

Gerber SA, et al. (2003). Absolute quantification of proteins and phosphoproteins from cell lysates by tandem Ms. Proc Natl Acad Sci 100(12):6940-5.

Hanke, S., et al. (2007). Absolute SILAC for accurate quantitation of proteins in complex mixtures down to the attomole level. J. Proteom Res, 7:1118-30.

Ciccimaro E., et al. (2009). Absolute quantification of phosphorylation on the kinase activation loop of cellular focal adhesion kinase by stable isotope dilution liquid chromatography/mass spectrometry. Anal. Chem. 2009, 81(9):3304-13.

Vinarov DA, et al. (2006). Wheat germ cell-free platform for eukaryotic protein production. FEBS J. 273(18):4160-9.

Tong KI, et al. (2012). Selective Isotope Labeling of Recombinant Proteins in *Escherichia coli*. Methods Mol Biol. 2896:439-48.

Mikami, S., et al. (2008). A human cell-derived in vitro coupled transcription/translation system optimized for production of recombinant proteins. Protein Expr. Purif. 62(2):190-8.

Mikami, S., et al. (2010). Cell-free protein synthesis systems with extracts from cultured human cells. Cell-Free Protein Production: Methods and Protocols, Methods in Molecular Biology, vol. 607.

Stergachis, A., et al. Rapid empirical discovery of optimal peptides for targeted proteomics. Nat. Meth. 2011, 8(12):1041-1043.

Kumar V., Barnidge D.R., Chen L.S., Twentyman J.M., Cradic K.W., Grebe S.K., Singh R.J. Quantification of serum 1-84 parathyroid hormone in patients with hyperparathyroidism by immunocapture in situ digestion liquid chromatography-tandem mass spectrometry. Clin Chem. 2010. 56(2):306-13.

Hanke, S., et al. (2008). Absolute SILAC for accurate quantitation of proteins in complex mixtures down to the attomole level. J. Proteom Res, 7:1118-30.

Vinarov DA, et al. (2006). Wheat germ cell-free platform for eukaryotic protein production. FEBS J. 273:4160-9.

(Continued)

*Primary Examiner* — Kagnew H Gebreyesus
(74) *Attorney, Agent, or Firm* — Thompson Hine LLP

(57) ABSTRACT

Methods for producing an isotope-labeled mammalian, including a human, biomolecule, such as polypeptides and proteins, in a cell-free protein synthesis system. A biomolecule standard is produced having at least one isotope different in abundance than that of the naturally occurring isotopes in the biomolecule. Methods for quantifying biomolecules standards expressed using mammalian cell-free extracts are disclosed. Methods for producing such standards, kits, systems and reagents, relating to the use of isotope-labeled biomolecule as quantification standards in mass spectrometric and nuclear magnetic resonance analysis.

21 Claims, 12 Drawing Sheets

(9 of 12 Drawing Sheet(s) Filed in Color)

(56) References Cited

OTHER PUBLICATIONS

Tong KI, et al. (2012). Selective Isotope Labeling of Recombinant Proteins in *Escherichia coli*. Methods Mol Biol. 896:439-48.

Mikami, S., et al. (2010). Cell-free protein synthesis systems with extracts from cultured human cells. Cell-Free Protein Production: Methods and Protocols, Methods in Molecular Biology, vol. 607, pp. 43-52.

Stergachis, A., et al. Rapid empirical discovery of optimal peptides for targeted proteomics. Nat. Meth. 2011, 8(12):1041-1043, doi:10.1038/nmeth.1770, 3 pages.

Yan et al. Control of PERK eIF2α kinase activity by the endoplasmic reticulum stress-induced molecular chaperone P58$^{IPK}$. PNAS 2002, 99(25):15920-15925.

Mikami et al. An efficient mammalian cell-free translation system supplemented with translation factors. Protein Expression and Purificaton 2006, 46(2):348-357.

Van Huizen et al. P58$^{IPK}$, a Novel Endoplasmic Reticulum Stress-inducible Protein and Potential Negative Regulator of eIF2α Signaling. Journal of Biological Chemistry, 2003, 278(18):15558-15564.

Davies et al. The E3L and K3L vaccinia virus gene products stimulate translation through inhibition of the double-stranded RNA-dependent protein kinase by different mechanisms. J. Virol. Mar. 1993; 67(3):1688-1692.

He et al. The $\gamma_1$34.5 Protein of Herpes Simplex Virus 1 Has the Structural and Functional Attributes of a Protein Phosphatase 1 Regulatory Subunit and Is Present in a High Molecular Weight Complex with the Enzyme in Infected Cells. Journal of Biological Chemistry, 1998, 273(33):20737-20743.

Novoa et al. Feedback Inhibition of the Unfolded Protein Response by *GADD34*-mediated Dephosphorylation of eIF2α. J Cell Biol, 2001,153(5):1011-1021.

Jousse et al. Inhibition of a constitutive translation initiation factor 2α phosphatase, *CReP*, promotes survival of stressed cells. J Cell Biol, 2003, 163(4):767-775.

Connor et al. Growth Arrest and DNA Damage-Inducible Protein GADD34 Assembles a Novel Signaling Complex Containing Protein Phosphatase 1 and Inhibitor 1. Mol Cell Biol, 2001, 21:6841-6850.

Egloff et al. Structural basis for the recognition of regulatory subunits by the catalytic subunit of protein phosphatase 1. EMBO J. 1997, 16(8):1876-1887.

Kebache et al. Nck-1 Antagonizes the Endoplasmic Reticulum Stress-induced Inhibition of Translation. Journal of Biological Chemistry, 2004, 279(10):9662-9671.

Kebache et al. Modulation of protein translation by Nck-1. PNAS 2002, 99(8):5406-5411.

Pereira et al. IMPACT, a Protein Preferentially Expressed in the Mouse Brain, Binds GCN1 and Inhibits GCN2 Activation. Journal of Biological Chemistry, 2005, 280(31):28316-28323.

Lopez et al. Selected reaction monitoring-mass spectrometric immunoassay responsive to parathyroid hormone and related variants. Clin. Chem., 2010, 56(2):281-290.

Origene, Heavy-labeled Full-length Protein as MS Standards: Accurate quantification of human protein biomarkers © 2013, http://www.origene.com/Mass_Spec_Std/, 2 pages.

RiNA GmbH, RTS Wheat Germ and RTS *E.coli* ( © 1999-2013), http://wwvv.rina-gmbh.de/index.php?id=100, 1 page.

Life Technologies, Cell-Free Expression Kits ( © 2013), http://products.invitrogen.com/ivgn/en/US/adirect/invitrogen?cmd=catDisplayStyle&catKey=8801&filterDispName=Cell-Free, 2 pages.

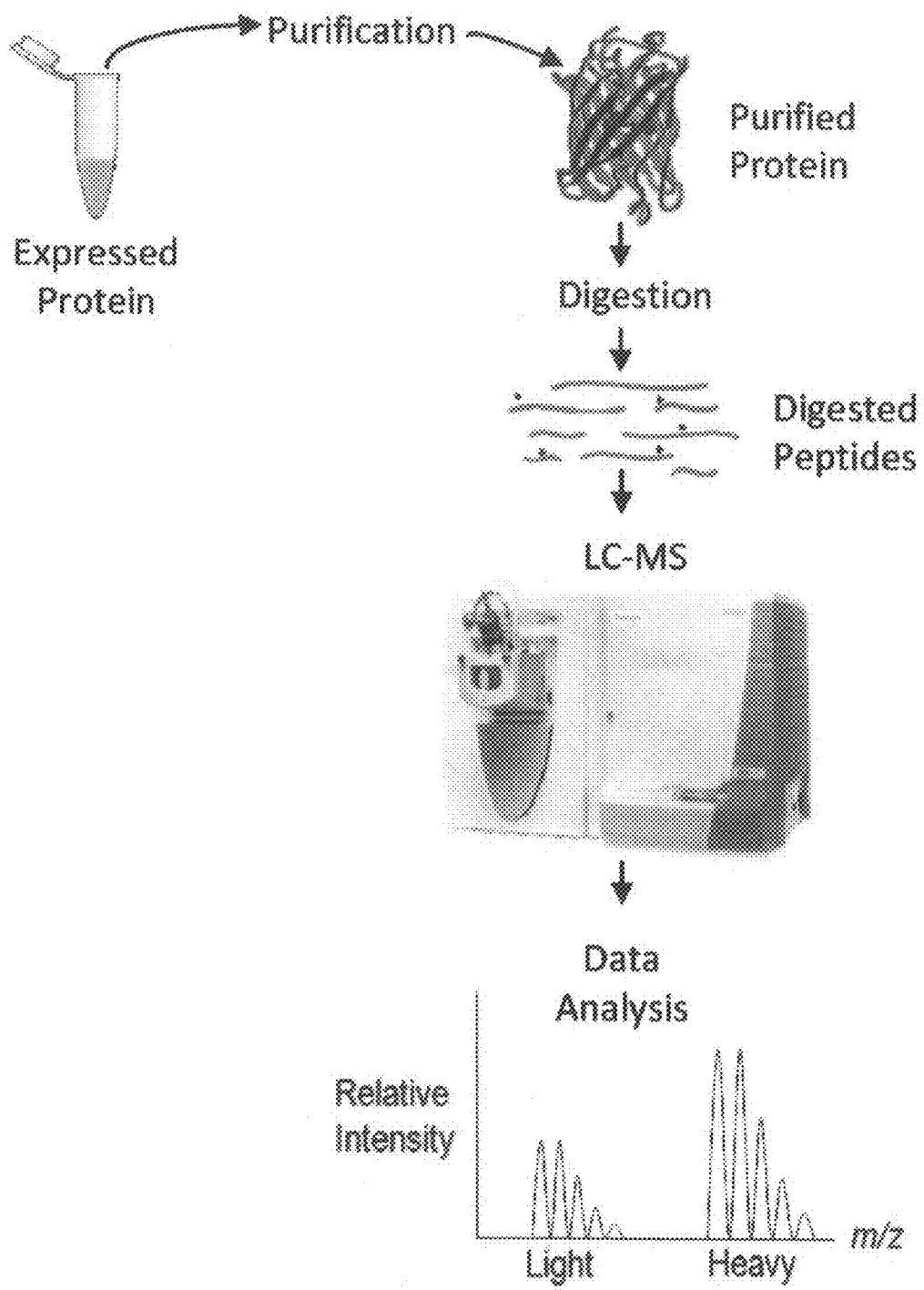

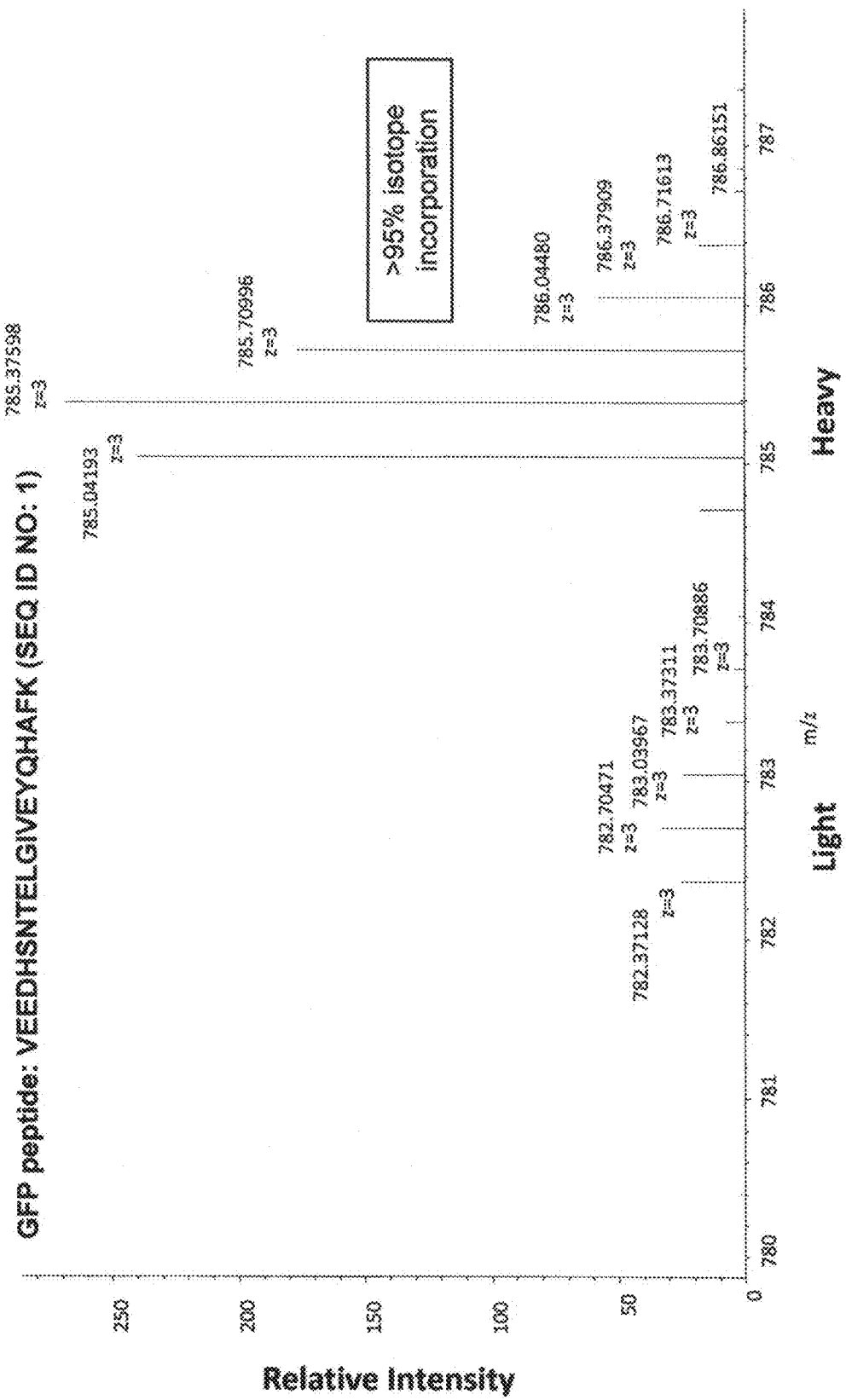

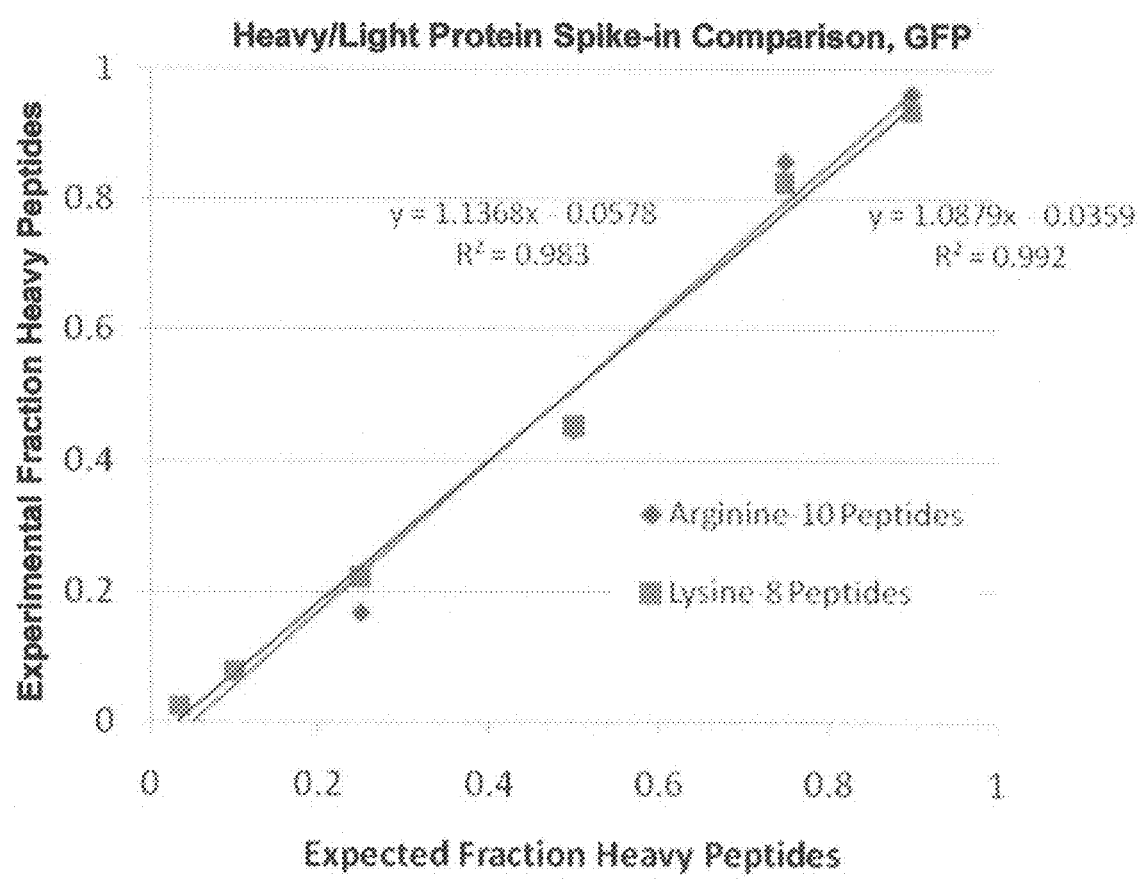

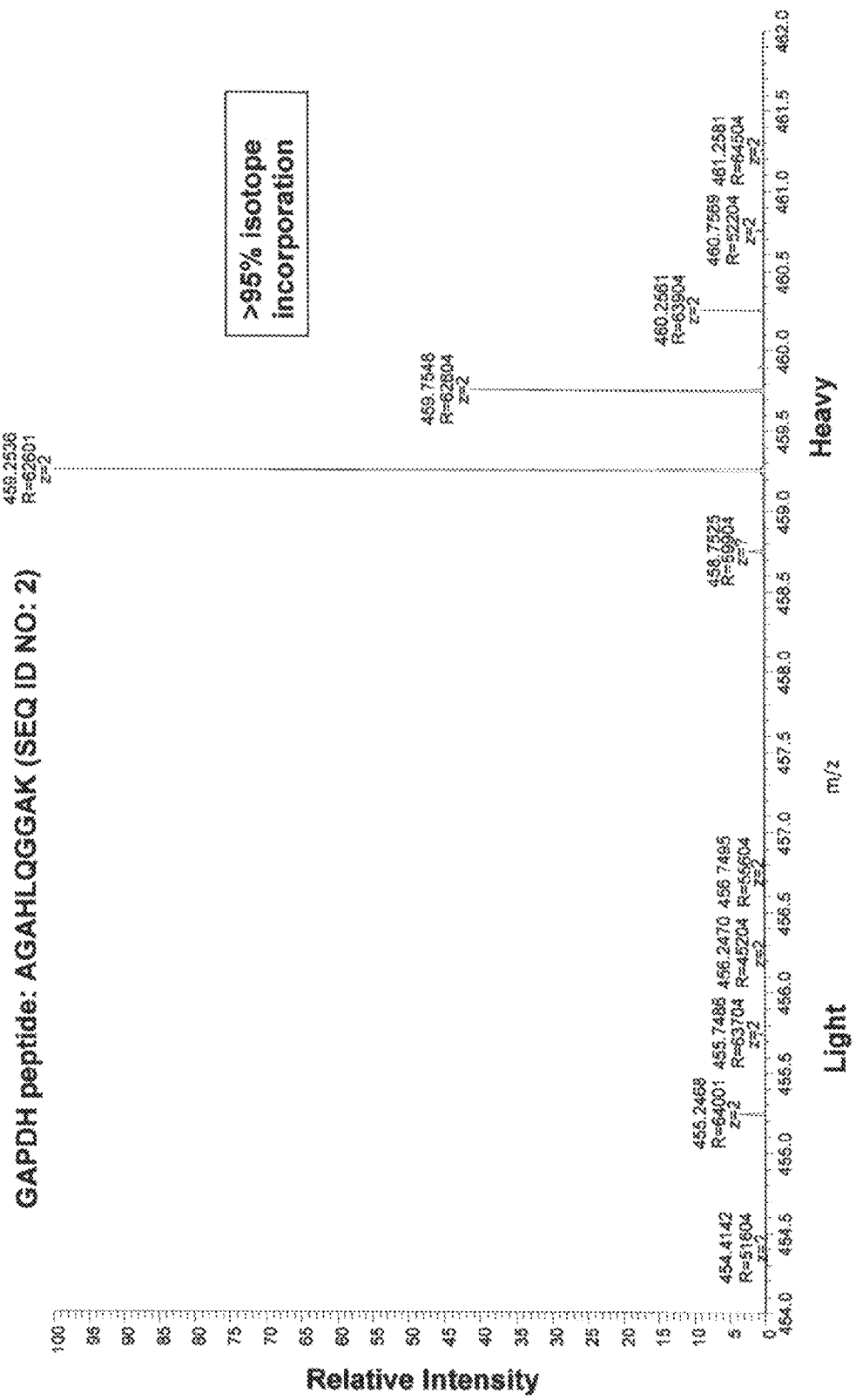

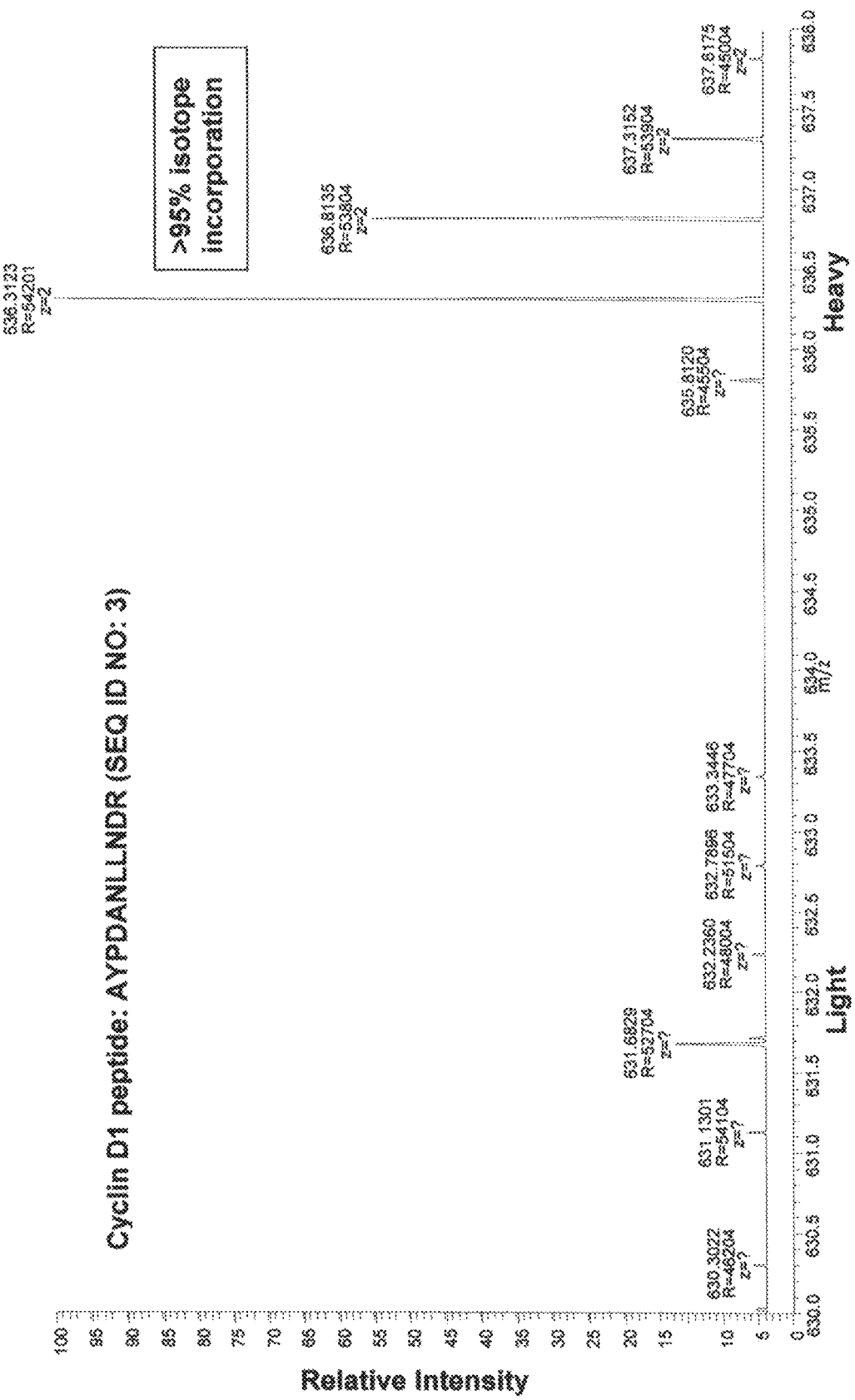

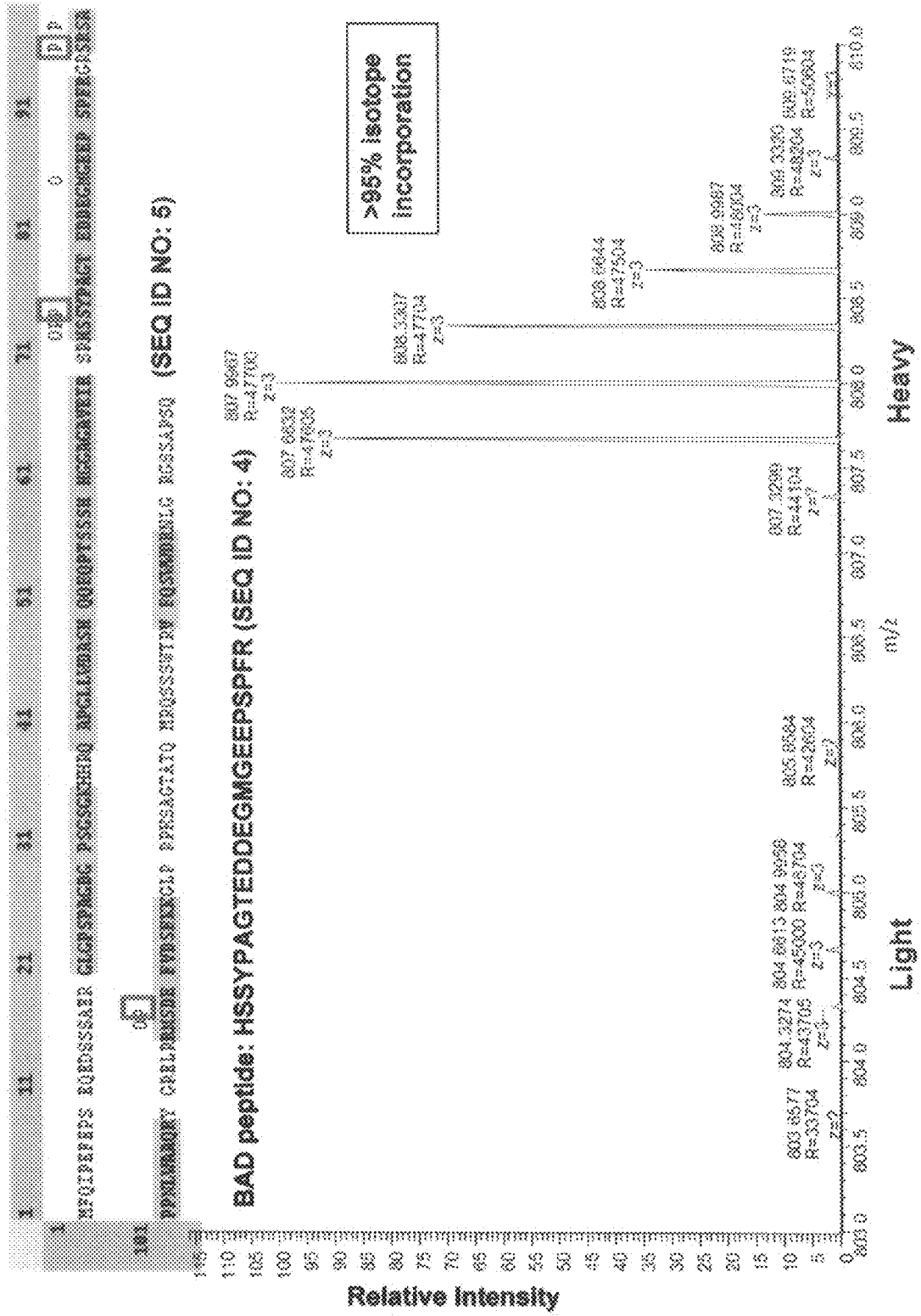

SEQUENCE LISTING

```
<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Val Glu Glu Asp His Ser Asn Thr Glu Leu Gly Ile Val Glu Tyr Gln
1               5                   10                  15

His Ala Phe Lys
            20

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Ala Gly Ala His Leu Gln Gly Gly Ala Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Ala Tyr Pro Asp Ala Asn Leu Leu Asn Asp Arg
1               5                   10

<210> SEQ ID NO 4
<211> LENGTH: 22
<212> TYPE: PRT
<213> ORGANISM: Artificial Sequence
```

```
<220> FEATURE:
<223> OTHER INFORMATION: Synthetic Construct

<400> SEQUENCE: 4

His Ser Ser Tyr Pro Ala Gly Thr Glu Asp Asp Glu Gly Met Gly Glu
1               5                   10                  15

Glu Pro Ser Pro Phe Arg
            20

<210> SEQ ID NO 5
<211> LENGTH: 168
<212> TYPE: PRT
<213> ORGANISM: Artificial Sequence
<220> FEATURE:
<223> OTHER INFORMATION: Synthetic Construct

<400> SEQUENCE: 5

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

METHODS FOR ISOTOPICALLY LABELING BIOMOLECULES USING MAMMALIAN CELL-FREE EXTRACTS

This application claims priority to U.S. application Ser. No. 61/514,695 filed Aug. 3, 2011, which is expressly incorporated by reference herein in its entirety.

Methods to produce an isotope-labeled protein and/or polypeptide in a cell-free in vitro protein synthesis system, i.e., either an in vitro translation system (IVT) or an in vitro coupled transcription/translation system (IVTT); the abbreviations are used interchangeably unless distinguished. A method for quantifying isotope-labeled protein and/or polypeptide standards for use as a relative or absolute standard in mass spectrometry (MS) analysis. A method for producing stable-isotope labeled proteins for nuclear magnetic resonance (NMR) analysis. A reagent kit for protein and/or polypeptide synthesis for performing cell-free in vitro protein synthesis and for quantifying isotope-labeled protein standards for use in MS and/or NMR.

Proteomics uses methods such as Western Blotting, enzyme linked immunosorbent assays (ELISA), NMR, and MS to understand protein structure, function, and interactions. MS can simultaneously identify proteins and protein post-translational modifications (PTM), but MS protein quantification requires the use of protein standards. One method for protein standard expression is in vitro coupled transcription/translation (IVT), in which a cellular extract system transcribes DNA into mRNA, which is subsequently translated into protein. Most IVT systems utilize prokaryotic (bacteria) or non-human eukaryotic (wheat germ or rabbit reticulocyte) cell extracts. These systems lack components needed for proper protein folding and proper post-translational modifications to result in biologically active human proteins.

MS is a powerful method to elucidate the composition of complex proteomic samples. Proteomic analysis has traditionally involved isolating proteins from biological samples, followed by fractionating the proteins using one- or two-dimensional gel electrophoresis. Fractionated proteins are subsequently analyzed by MS, either intact proteins using "top down" methods, or proteins that have been enzymatically digested into peptides in "bottom up" analysis. Relative differences between samples can be measured semi-quantitatively, either by assessing gel band or spot staining intensity, or by the number of MS spectra. These label-free methods are, however, highly variable due to differences in peptide ionization efficiency. In addition, proteomic samples typically have a large dynamic range of protein abundance with high heterogeneity, resulting in significant under-sampling using gel-based analysis and MS instruments with lower sensitivity and duty cycle.

Isotopically-labeled internal standards are required to accurately quantify differences in samples analyzed by MS. If the internal standard concentration is known, isotopically-labeled internal standards permit a standard curve to be generated to determine the absolute concentration of analyte in the sample. Internal standards for MS analysis ideally are biologically and chemically indistinguishable from the analyte to be measured.

Isotopes have traditionally been incorporated into peptide and protein standards by numerous chemical, enzymatic, and metabolic labeling methods. One common labeling method uses chemically synthesized isotope-labeled peptides for absolute quantitation, i.e., AQUA method. The AQUA method introduces known quantities of isotope-labeled peptides into biological samples to be analyzed, permitting the relative quantification of unlabeled peptides. Absolute quantitation can be accomplished by classic isotope dilution measurements, where stable isotope-labeled peptides are used to generate a standard curve.

Alternatively, peptides in a sample can be labeled using isotopic or isobaric chemical tags, e.g., isotope dimethylation, iCAT, iTRAQ or TMT reagents to create internal reference peptide standards for relative quantitation. These methods conjugate and/or covalently attach chemical tags to peptides and/or proteins.

Enzymatic methods for isotope labeling generally add $^{18}O$ isotopes to peptide carboxyl termini through tryptic digestion in $^{18}O$-labeled water. Stable isotopes can be metabolically incorporated into proteins in cell culture (stable isotope cell culture, SILAC). SILAC methods use metabolic incorporation into proteins of heavy isotope-labeled amino acids or non-heavy isotope-labeled, i.e., unlabeled or light, amino acids. Heavy isotopes that can be used are stable isotopes such as, but not limited to, $^{13}O$, $^{15}N$, $^{74}Se$, $^{76}Se$, $^{77}Se$, $^{78}Se$, $^{82}Se$, $^{18}O$, and $^{2}H$. An example of the SILAC technique used for metabolic incorporation of isotopes uses *Escherichia coli* (*E. coli*) cultured with media supplemented with heavy isotope-labeled amino acids to express isotope-labeled proteins or concatenated polypeptides (QConCat).

Although both peptide and protein isotope-labeled standards are applicable for relative and absolute MS quantitation, protein standards have benefits over peptide standards. In a majority of MS sample preparation workflows, proteins are extracted from cells or tissues before fractionation and enzymatic digestion. Protein standards can be added to samples immediately after cell lysis and before any additional sample preparation, which results in less variance from sample processing. Protein standards provide an added control for enzymatic digestion efficiency. Upon digestion, protein standards also provide multiple peptides that can be used for quantitation without prior knowledge of which peptide may give the best MS signal. Depending on the protein source, protein standards may also contain post-translational modifications that can be monitored.

Current methods to isotopically label proteins are limited. SILAC labeling incorporates heavy isotope-labeled amino acids into proteins; however, it has disadvantages for making routine protein standards. Because SILAC is an in vivo metabolic method that labels all proteins, it is costly and wasteful for expression of individual isotopically-labeled protein standards. Although SILAC is amenable to whole organism labeling (e.g. bacteria, yeast, worms, mice), human protein standards are limited to those expressed in tissue cultured cell lines. Expression of recombinant proteins in SILAC cells has been used to increase the diversity of proteins that can be labeled by SILAC; however, many proteins that are toxic or result in cell cycle arrest or apoptosis cannot be expressed in vivo. Isotope scrambling of amino acids has been observed for many cell lines used for SILAC. This phenomenon has been shown to be caused by heavy isotope-labeled amino acid catabolism, and is especially common for heavy isotope-labeled arginine, which can be converted to heavy isotope-labeled proline by arginine dehydrogenases.

In vitro expression using cell-free extracts is another method to generate isotope-labeled proteins. This method allows expression of a variety of recombinant proteins, including many that cannot be expressed in vivo. Cell-free expression typically does not suffer from isotope scrambling observed during in vivo SILAC methods because stable isotope incorporation can be limited to recombinant proteins of interest and takes less than 24 hours. Two cell-free systems used for isotopic labeling of protein are *E. coli* and wheat germ extracts; both systems express protein standards with isotope incorporation up to 95% into only the expressed recombinant protein. Although E. coli and wheat germ extracts can be scaled to express moderate amounts, e.g., 0.1 mg-10 mg of protein standard, they are inadequate for expressing many mammalian proteins. Both systems are derived from simple organisms that have different amino acid codon usage compared to complex mammalian genomes, so expression constructs may have to be codon optimized to maximize expression in these systems. Endogenous chaperones in these systems are not suited for the correct folding of mammalian proteins, leading to mis-folded proteins and protein aggregation. Proteins expressed in E. coli and wheat germ extracts are typically missing normal post-translational modifications, including phosphorylation and glycosylation, which may be required for protein function or protein-protein interactions. These features may be important to generate an isotopically-labeled protein standard that is the most biologically equivalent to the proteins of mammalian proteomes.

Peptide standards remain the predominant standard used for relative and absolute quantitation, despite advantages of protein standards over peptide standards. The main reason for this is due to a lack of isotopically-labeled standards for all proteins, where peptides can be readily chemically synthesized. Protein standards are difficult to quantify because they typically must first be purified to homogeneity and then measured using either absorbance at 280 nm ($A_{280}$) or a protein assay. Both techniques have high protein to protein variability. $A_{280}$ measurements require a known molar extinction coefficient unique to each protein or protein isoform to determine protein concentration. Protein assays such as Bradford, Lowry, and bicinchoninic acid (BCA) have been used to quantify purified proteins, but can give widely different results depending on the amino acid composition of the protein. In contrast, peptide standards can be readily measured using small amounts of peptide by amino acid analysis (AAA) to determine peptide composition and concentration.

Stable, isotopically-labeled protein standards represent the "gold standard" for targeted MS proteomics quantitation. Heavy labeled standards are required for clinically validated assays, but production of heavy proteins is costly and most widely demonstrated through in vivo SILAC methods. A human-cell derived in vitro protein expression system is available (Pierce Biotechnologies, Rockford Il.) that produces higher yields of expressed proteins and improves post-translational modifications such as phosphorylation and glycosylation compared to other eukaryotic and prokaryotic systems. Because proteins produced using this system are more biologically equivalent to the proteins of mammalian proteomes, the disclosed system can improve isotopically-labeled mammalian protein standards if heavy labeled components such as amino acids or tRNAs could be introduced to replace or compete out endogenous light components of the lysate.

A human-cell derived in vitro protein expression system is disclosed. This system provided higher yields of expressed proteins and significant improvement of post-translational modifications, such as phosphorylation and glycosylation, compared to other eukaryotic and prokaryotic systems. Proteins produced using the disclosed method were more biologically equivalent to the proteins of mammalian proteomes compared to other methods. The disclosed method was used to make improved isotopically-labeled protein standards by introducing heavy labeled components, such as amino acids and/or tRNAs, to replace or compete with endogenous non-heavy labeled components of the lysate, also termed light components of the lysate.

Using a cell lysate that was derived from SILAC-labeled HeLa cells, having a high probability of producing an isotopically-labeled protein, endogenous amino acids (L-lysine or L-arginine) and tRNAs linked to these amino acids were assumed to be isotopically labeled after 4-5 cell doublings of cells grown in media containing only $^{13}C_6^{15}N_2$ L-lysine-2HCl and/or $^{13}C_6^{15}N_4$ L-arginine-HCl. Upon verification that all proteins in the HeLa cells were >98% labeled using SILAC, a lysate was prepared using standard methods developed for a coupled in vitro transcription/translation (IVT) system. Test expression of a model protein, histidine-tagged green fluorescent protein (HIS-tagged GFP), confirmed that the heavy isotope-labeled lysate was capable of protein expression; however, protein expression yields were about 5-fold less than control unlabeled lysates. This result was reproducible, appeared to be a consequence of poorer cell health before lysate production, and may be linked to use of dialyzed fetal bovine serum (FBS) required for the SILAC method. Despite the low yield of HIS-tagged GFP expression using heavy isotope-labeled lysates, the average isotope incorporation for GFP protein, based on MS of tryptic peptides, was >95% when protein was expressed using extracts supplemented with additional heavy isotope-labeled amino acids and when exogenous tRNAs were omitted.

These results demonstrated production of a heavy isotope-labeled protein using a costly and inefficient human IVT system: the entire lysate, instead of only the expressed protein, was heavy isotope-labeled while labeling of only the expressed protein is required for production of a protein standard. Using as controls heavy lysates supplemented with light amino acids, and normal light lysates supplemented with heavy amino acids, about 30-40% isotope was incorporated for both controls after MS analysis of HIS-tagged GFP. Omission of exogenous tRNAs increased isotope incorporation by an additional 10%, to a final average incorporation of 50%. These levels of incorporation were not expected, because traditional prokaryotic and eukaryotic IVT systems typically have <5% isotopically-labeled amino acid incorporation unless they are modified. A published modification method removed endogenous free amino acids by desalting or dialyzing the lysates. Another used ion exchange chromatography to remove endogenous tRNAs, which may be charged with light amino acids. However, this tRNA-depleted lysate must be supplemented with exogenous tRNAs and amino acids for protein synthesis.

By titrating the amount of heavy amino acids added to light lysates, the isotope incorporation efficiency of expressed HIS-tagged GFP was increased to >95% at heavy amino acid ($^{13}C_6^{15}N_2$ L-lysine-2HCl and/or $^{13}C_6^{15}N_4$L-arginine-HCl) final concentrations >1 mM. This result was not expected; the concentration of the amino acid supplement was 2 mM and was believed not to be limiting, i.e., it was in excess, for production of proteins in the disclosed coupled-IVT system. The same results from HIS-tagged GFP were obtained using amino acid titration with another protein, hemagglutinin (HA)-tagged Bcl-2-associated death promoter (BAD).

Using the disclosed methods, the following proteins were expressed with isotope incorporation efficiencies >95%: AKT1, tumor protein 53 (TP53), glyceraldehyde 3-phosphate dehydrogenase (GAPDH), parathyroid hormone (PTH), retinoblastoma (RB), human chorionic gonadotropin (hGCβ), cyclin D1 (CCND1) and 3-phosphoinositide dependent protein kinase-1 (PDPK1). Supplementing the reactions with light amino acid mixture absent lysine and/or arginine, termed a drop out mixture, was not necessary for robust protein expression or for heavy isotope incorporation. The disclosed method was less expensive than using a heavy labeled-isotope labeled lysate. The disclosed method was demonstrated for over ten different proteins.

During purification of over-expressed heavy HA-BAD protein, two additional proteins co-purified. Using MS, these proteins were determined to be 14-3-3 proteins, which are known to form a heterodimeric complex with phosphorylated BAD and which have numerous sites of modification including sites known to be required for 14-3-3 protein binding. These findings demonstrated that the proteins that were expressed using the inventive heavy IVT system were functional; they were modified and integrated into protein complexes.

Human PTH was expressed using the inventive method as an internal standard (spike) for a MS immunoprecipiation assay. A typical yield of heavy isotope-labeled proteins expressed using the coupled human IVT or IVTT systems is 40 μg/ml to 80 μg/ml in 8-10 hours. In contrast, a high yield-coupled-IVT or IVTT system can produce >100 μg/ml heavy proteins since protein expression continues for up to 16 hr. Higher amounts of protein are required for NMR protein structure applications. NMR typically requires proteins with all carbons or nitrogens isotopically labeled for analysis, i.e., total protein labeling of all amino acids. The inventive high yield method is useful for MS structural analysis, which typically requires 10 μg-100 μg purified isotope-labeled protein. For a high-yield system, the IVT reaction was performed in a dialysis chamber that was seated in a tube containing additional small molecules (nucleotides, ATP, salts, and amino acids) in a dialysate. In contrast to the smaller scale coupled IVT reactions, high-yield expression required additional amino acids.

A custom dialysate was prepared containing a light amino acid mixture without L-lysine and L-arginine to supplement with $^{13}C_6^{15}N_2$ L-lysine-2HCl and $^{13}C_6^{15}N_4$ L-arginine-HCl. GFP and three different human proteins were expressed with GFP heavy isotope incorporation determined to be >97% by MS analysis, as shown in FIG. 6.

The disclosed method produced an isotope-labeled protein in a mammalian cell-free expression system. The disclosed method quantified isotope-labeled protein standards for use as a relative or absolute standard with MS. The disclosed kit was used for protein synthesis using the disclosed method, and the mammalian proteins synthesized contained post-translational modifications, such as glycosylation and phosphorylation, evidencing that the method resulted in an intact, functional mammalian protein.

BRIEF DESCRIPTION OF THE DRAWINGS

The patent or application file contains at least one drawing executed in color. A Petition under 37 C.F.R. §1.84 requesting acceptance of the color drawing is being filed separately. Copies of this patent or patent application publication with color drawing(s) will be provided by the Office upon request and payment of the necessary fee.

FIGS. 1A and 1B schematically show heavy isotope-labeled recombinant protein expression, purification, and mass spectroscopy (MS) analysis.

FIGS. 2A-2D show isotope-labeled green fluorescent protein (GFP) expression using human IVT extracts using different human in vitro translation extracts, also referred to as lysates.

FIG. 4 shows linearity of MS quantification using a heavy isotope-labeled protein standard, stable isotopically-labeled GFP, as a standard for MS quantitation of a non-heavy-isotope labeled or light GFP standard dilution.

FIGS. 5A-D show IVT expression of isotopically-labeled human proteins.

FIGS. 6A-B show expression of a heavy isotope BAD protein and MS analysis.

Figure 1A:
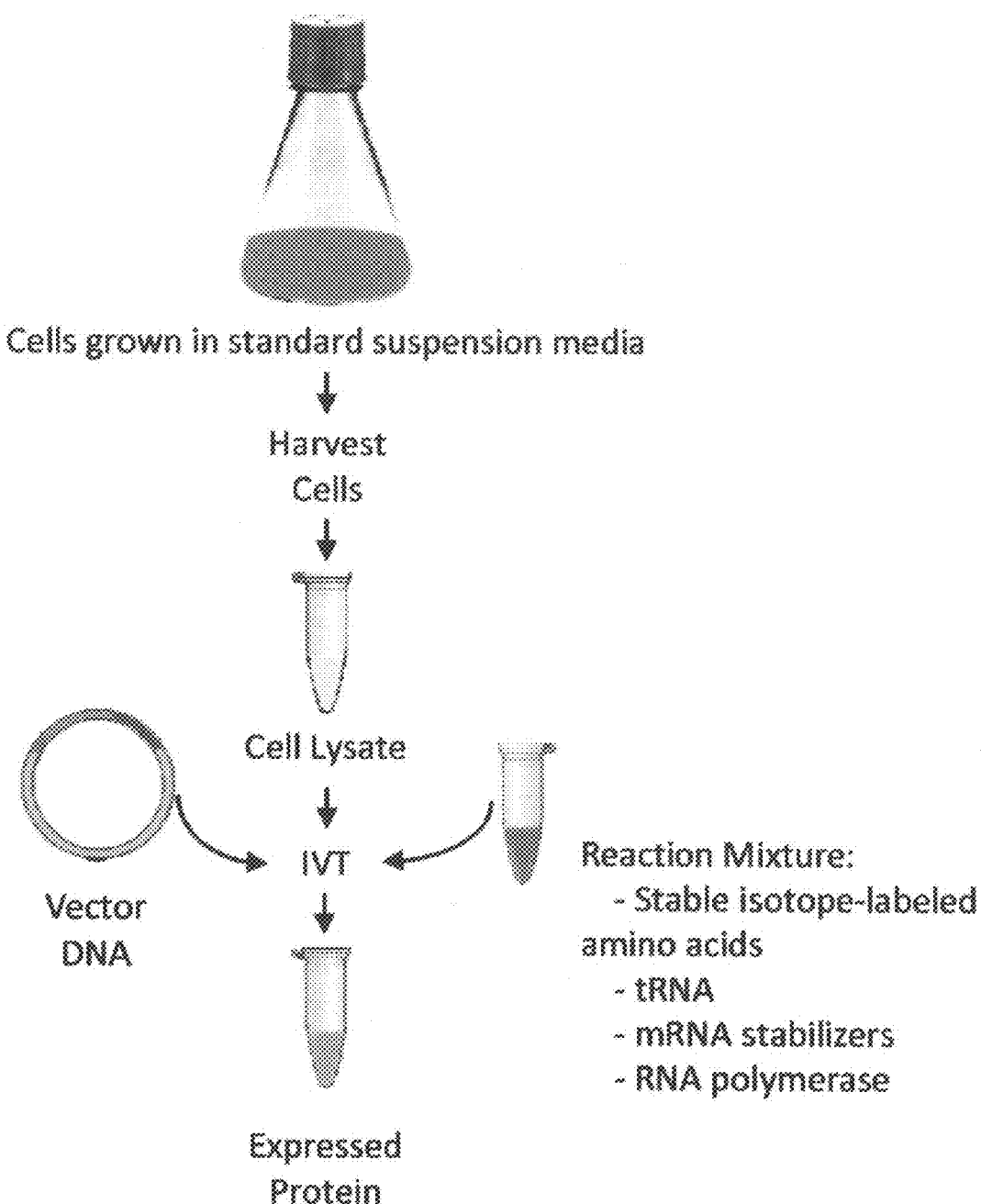

Methods and kits to produce and quantify isotopically-labeled biomolecules, such as polypeptides and proteins, for use as standards for relative and absolute quantitation of samples by mass spectrometry (MS). A method for producing isotope-labeled biomolecules, such as polypeptides and proteins, using a mammalian cell-free protein synthesis system. One embodiment is a method that produces a biomolecule standard having at least one isotope different in abundance than that of the naturally occurring isotopes in the biomolecule of interest. One embodiment is a method that produces an isotope-labeled protein using a mammalian cell-free extract, also termed a cell lysate. One embodiment is a mammalian cell-free extract derived from human cells.

One embodiment is an in vitro method for producing heavy isotope-labeled proteins by translating an mRNA template, i.e., an in vitro translation method. This embodiment combined a mammalian cell-free extract with at least one mRNA, a plurality of accessory expression proteins, an ATP regeneration system, and heavy isotope-labeled amino acids to form an in vitro translation system, which is incubated under conditions to result in production of at least one heavy isotope-labeled protein from the mRNA.

One embodiment is an in vitro method for producing heavy isotope-labeled protein by transcribing a DNA template and then translating the resultant mRNA, i.e., a coupled in vitro transcription/translation method. This embodiment combined a mammalian cell-free extract with at least one DNA, at least one RNA polymerase, a plurality of accessory expression proteins, an ATP regeneration system, and a plurality of heavy isotope-labeled amino acids and/or heavy isotope-labeled tRNAs to form an in vitro transcription/translation system, which was incubated under conditions to result in production of at least one heavy isotope-labeled protein from the DNA. To increase efficiency of translation, in one embodiment the mammalian cell-free extract was preincubated for at least one minute with at least one accessory protein and a plurality of heavy isotope-labeled amino acids and/or heavy isotope-labeled tRNAs. Then, and without removing any component, DNA, RNA polymerase, and an ATP regeneration system were added to form an in vitro transcription/translation system, which was incubated under conditions to result in production of at least one heavy isotope-labeled protein from the DNA. This method of preincubation of the accessory proteins with the mammalian cell-free extract and the subsequent addition of heavy amino acids and DNA has been shown in the art to prevent phosphorylation of eukaryotic translation initiation factor 2A (EIF2A). This is necessary for high level IVT and IVTT protein expression using HeLa cell extracts.

One embodiment is an in vitro method for producing heavy isotope-labeled protein using a coupled transcription/translation system. This embodiment combined a mammalian cell-free extract with at least one DNA, at least RNA polymerase, an ATP regeneration system, a plurality of non-heavy isotope-labeled amino acids and/or non-heavy isotope-labeled tRNAs, and then added a plurality of heavy isotope-labeled amino acids and/or heavy isotope-labeled tRNAs in a concentration sufficient to replace the non-heavy isotope-labeled amino acids and/or non-heavy isotope labeled tRNAs to form an in vitro transcription/translation system, which was incubated under conditions to result in production of at least one heavy isotope-labeled protein from the DNA. This method resulted in increased protein expression over time. Such methods supplementing tRNAs charged with heavy amino acids increased isotope incorporation efficiency to >50%, >95%, >97%, and >99% in embodiments. Necessary reaction mix components present in the dialysate continuously exchanged into the IVT reaction lysate through the dialysis membrane, and potential translation inhibitory compounds were diluted from the lysate by dialysis.

Accessory expression proteins are known to one skilled in the art. They include, but are not limited to, P58$^{IPK}$ and BiP (Yan et al. PNAS 2002, 15920; Van Huizen J. Biol. Chem., 2003, 15558), eIF2, eIF2B, eIF4E, and p97 (Mikami et al Protein Expr Purif. 2006, 46(2):348-57), K3L and E3L (Davies et al. J. Virol. 1993 March; 67(3):1688-92), $\gamma_1$34.5 (He et al. J. Biol. Chem., 1998, 273: 20737), GADD34 (Novoa et al. J Cell Biol, 2001, 1011; Jousse et al. J Cell Biol, 2003, 767), CReP (Jousse et al. J Cell Biol, 2003, 767; Connor et al. Mol Cell Biol, 2001, 6841), PP1 regulatory subunit (Egloff et al. EMBO J 1997, 1876), Nck-1 (Kembache et al. JBC, 2004 9662; Kembace et al PNAS 2002, 5406), IMPACT (Pereira JBC, 2005, 28316), eIF2B (Kembache et al. J. Biol. Chem., 2004 9662).

An ATP-regeneration system is known in the art and includes creatine kinase (CK) and creatine phosphate. Additional supplemental nucleotides required for in vitro transcription and translation include adenosine triphosphate (ATP), cytosine triphosphate (CTP), guanidine triphosphate (GTP), and uracil triphosphate (UTP).

In any of the disclosed embodiments, the cell-free extract can be prepared using cultured cells, e.g., 3T3 mouse cells, Chinese hamster ovary (CHO) cells, etc., known to one skilled in the art. The cultured cells may be human-derived. The cultured cells may be grown in media containing heavy isotope-labeled amino acids.

The heavy isotope may be an isotope that is different in abundance than the naturally occurring isotope. The final concentration of the heavy isotope-labeled amino acid in the in vitro translation system may be 0.05 mM to 4 mM. The final concentration of the heavy isotope-labeled amino acid in the coupled in vitro transcription/translation system may be 0.5 mM to 4 mM. The heavy isotope may be a stable isotope selected from, e.g., $^{74}$Se, $^{76}$Se, $^{77}$Se, $^{78}$Se, $^{82}$Se, $^{15}$N, $^{13}$C, $^{18}$O, and $^{2}$H.

In any embodiment of the inventive method, the incorporation efficiency of the heavy isotope-labeled amino acid ranged from 10% to 100%.

In any embodiment using a coupled in vitro transcription/translation system, the method may be performed in a dialysis chamber. This resulted in relatively higher yield of the at least one heavy isotope-labeled protein from the DNA, compared to incubation not in a dialysis chamber. The heavy isotope-labeled amino acids were added to the external dialysate containing additional limiting reaction components such as salts, nucleotides, tRNAs, and additional non-heavy isotope-labeled amino acids. In this method, IVT reactions expressed proteins for longer periods of time, resulting in higher protein yield.

Uses of the heavy isotope-labeled protein include, but are not limited to, the following uses. The heavy isotope-labeled protein may be purified. The heavy isotope-labeled protein may be quantitated, either before or after purification. As one example, a fluorescent protein tag may be part of the expressed protein sequence, and fluorescence may be determined using standard methods known in the art to quantitate the expressed protein. As one example, the heavy isotope-labeled protein may be quantitated by mass spectroscopy using at least one reference peptide from the protein or from a protein tag. The heavy isotope-labeled protein may be quantitated by, e.g., enzyme linked immunosorbent assay (ELISA), Western blot, and/or antibody-based quantitative assay, as known in the art. The purified heavy isotope-labeled protein may be quantitated by a protein assay method, e.g., Bradford assay, bicinchoninic acid (BCA) assay, and/or Lowry assay, as known in the art.

The heavy isotope-labeled protein may be used a standard for quantitative MS. The heavy isotope-labeled protein may be used for NMR structural analysis. The heavy isotope-labeled protein may be used to assess relative recovery of a corresponding native and heavy isotope-labeled protein during lysis, fractionation, enrichment, purification, immunoprecipitation, etc. The heavy isotope-labeled protein may be used to assess relative digestion efficiency of a native protein and the heavy isotope-labeled protein. The heavy isotope-labeled protein may be used to assess relative post-translational modification of a native protein and the heavy isotope-labeled protein by, e.g., a post-translational protein modification enzyme, such as a protease, a kinase, a phosphatase, an acyl transferase, and/or a ligase.

One embodiment is a kit for producing heavy isotope-labeled proteins. Kit components of an in vitro translation system include a mammalian cell-free extract, a plurality of accessory expression proteins, an ATP regeneration system, a plurality of heavy isotope-labeled amino acids, and instructions for using the kit to form an in vitro translation system. Kit components of a coupled in vitro transcription/translation system include a mammalian cell-free extract, an RNA polymerase, a plurality of accessory expression proteins, an ATP regeneration system, a plurality of heavy isotope-labeled amino acids, and instructions for using the kit to form an in vitro transcription/translation system.

One embodiment is a kit for producing heavy isotope-labeled proteins in a dialysis chamber. Kit components include a mammalian cell-free extract, an RNA polymerase, a plurality of accessory expression proteins, an ATP regeneration system, a plurality of heavy isotope-labeled amino acids, and instructions for using the kit to form an in vitro transcription/translation system in a dialysis chamber.

Methods for quantifying biomolecules standards expressed using mammalian cell-free extracts. One embodiment is a method quantifying a protein standard using a protein assay. One embodiment is quantifying a protein standard using an assay such as absorbance at 280 nm ($A_{280}$), Bradford assay, Lowery assay, BCA assay, or 660 nm assay. One embodiment is a method quantifying a protein standard using a fluorescent assay. One embodiment is quantifying a protein standard that is a fluorescent protein. One embodiment is quantifying a protein standard that is expressed with a fluorescent tag. One embodiment is a protein standard where the fluorescent tag is a fluorescent protein. One embodiment is a protein standard where the fluorescent tag is GFP. One embodiment is quantifying a recombinant protein standard using a reference peptide. One embodiment is using a peptide from the protein standard sequence as a reference peptide. One embodiment is using a peptide co-expressed with the protein standard as a reference peptide.

Methods for quantifying isotope-labeled protein standards for use as a relative or absolute standard with mass spectrometry. One embodiment mixes a stable isotope-labeled protein standard with a sample containing the protein of interest to be measured. In one embodiment, a stable isotope-labeled protein standard is not purified before mixing with samples containing the proteins to be measured by relative and/or absolute abundance. In one embodiment, a stable isotope-labeled protein standard is purified before mixing with samples containing the proteins to be measured by relative abundance. In one embodiment, a stable isotope-labeled protein standard is serially diluted to create a standard curve for absolute quantitation. In one embodiment, a stable isotope-labeled protein standard is serially diluted before mixing with unlabeled samples.

In one embodiment, the disclosed isotope-labeled proteins produced with an IVT system were purified from the IVT reaction mixture prior to use as a MS protein standard. In one embodiment, the disclosed isotope-labeled proteins produced with an IVT system were unpurified from the IVT reaction mixture prior to their use as a MS protein standard. In one embodiment, the isotope-labeled protein was quantitated, e.g., by MS or by measuring fluorescence of the isotope-labeled protein. In one embodiment, the IVT reaction mixture or an aliquot of the IVT reaction mixture was "spiked", i.e., supplemented, with a known quantity of a heavy labeled peptide, and the "spiked" IVT reaction mixture was then analyzed by MS to quantitate the isotope-labeled protein based on a comparison to the heavy labeled peptide. In one embodiment, the "spiked" peptide had a fluorescent tag and the isotope-labeled protein also had a fluorescent tag, allowing the absolute quantity of the IVT-expressed protein to be determined by comparing the fluorescent intensities of the "spiked" peptide and the expressed protein from the IVT reaction mixture. In one embodiment, the heavy proteins were "spiked" in whole. In one embodiment, the heavy peptides were "spiked" pre-digested by, e.g., exposing the IVT reaction mixture to a proteolytic enzyme (e.g., trypsin) or a proteolytic agent, to determine digestion efficiency. In one embodiment, digestion efficiency ranged from 10% to 100%. By determining the amount of the expressed isotope-labeled protein in the IVT reaction mixture, the unpurified expressed isotope-labeled protein in the IVT reaction mixture was used to "spike" an unknown sample and therefore, be used as a quantitative internal standard.

One embodiment is a reagent kit for protein synthesis for implementing the disclosed method. The kit may include, as known to one skilled in the art, the following components at concentrations adequate for protein synthesis, a cell-free extract, accessory proteins, RNA polymerase, nucleotide mixture, a mixture of ATP, creatine phosphate, and creatine phosphokinase ("energy" mixture), salts, RNAse inhibitors, tRNA amino acid mixture, stable isotope-labeled amino acids, and nuclease-free water, with instructions for performing the method.

FIGS. 1A and 1B schematically show use of a human cell extract in in vitro protein expression (IVT). Heavy isotope-labeled recombinant protein expression, purification, and mass spectroscopy (MS) analysis are shown. HeLa cells were grown in a standard suspension media, then harvested, and a cell-free extract or lysate was obtained. In FIG. 1A, cells were cultured with normal or SILAC media, harvested, and lysed to prepare cell lysates. Lysates were combined with reaction mixture, vector DNA, and stable isotope-labeled amino acids to express recombinant proteins in an IVT reaction. The expressed protein was purified, digested into peptides, and analyzed by LC-MS (FIG. 1B). Percent incorporation of stable-isotopes was based on ratio of areas under the curve (AUC) for heavy and light isotopically-labeled peptides.

Cells were cultured and lysate prepared as follows. HeLa cells (ATCC CCL-2.2) were grown in suspension using SMEM supplemented with 10% FBS. For stable-isotope labeling using amino acids in cell culture (SILAC), HeLa cells were grown in custom SMEM media supplemented with $^{13}C_6^{15}N_2$ L-Lysine, $^{13}C_6^{15}N_4$ L-arginine and 10% dialyzed FBS. Cell-free extracts were prepared by exposing cells to nitrogen under hyperbaric conditions (300 psi), followed by release from a PARR non-stirred pressure vessel at a constant rate.

Isotopically-labeled proteins were expressed in IVT reactions using a custom amino acid mix supplemented with stable isotope-labeled amino acids $^{13}C_6^{15}N_2$ L-Lysine and $^{13}C_6^{15}N_4$ L-arginine. All reactions were incubated at 30° C. for up to 16 hours. Recombinant HIS-GFP protein fluorescence was measured using a GFP standard curve with a Tecan Safire fluorometer and purified using the Pierce HisPur Cobalt Resin Purification Kit™ (Pierce Biotechnologies, Inc. Rockford Il.). Recombinant HA-tagged proteins were assessed by Western blotting using anti-HA antibodies and purified using the HA Tag IP/Co-IP Kit (Pierce Biotechnologies, Inc.).

Samples were prepared and subjected to LC-MS as follows. Purified protein samples were separated by SDS-PAGE and stained using GelCode® Blue Stain Reagent (Pierce Biotechnologies, Inc.). Gel slices containing each protein were destained, reduced and alkylated, before digestion to peptides. Digestion occurs by exposure to a proteolytic enzyme (e.g., trypsin) or other proteolytic agent. In this case, digestion was performed using trypsin for 4-16 hours. After digestion, the peptides were desalted using Proxeon Stage C18 micro-column tips (Thermo Fisher Scientific, Inc.) and reconstituted with 0.1% TFA.

For peptide analysis, a NanoLC-2D™ high-pressure liquid chromatograph (HPLC) (Eksigent) with a PicoFrit™ C18 column 75 µm ID×20 cm (New Objective) was used to separate peptides using a 5%-40% gradient (A: water, 0.1% formic acid; B: acetonitrile, 0.1% formic acid) at a flow rate of 300 mL/min for 40 min. A Thermo Scientific LTQ Orbitrap XL ETD Mass Spectrometer was used to detect peptides using a top six experiment consisting of single stage MS followed by acquisition of six MS/MS spectra with collision induced dissociation (CID) for protein identification.

Using the Thermo Scientific Proteome Discoverer™ 1.3 software, CID spectra were searched using the SEQUEST® search engine against a custom human SWISProt database. Static modification included carbamidomethyl with methionine oxidation, Lysine-8 and Arginine-10 used as dynamic modifications. SILAC ratios were based on the area under the curve (AUC) for each heavy and light peptide and used to determine stable isotope incorporation.

To measure protein abundance using MS, heavy protein standards are required to accurately quantify the amounts of unlabeled, endogenous proteins in samples. Ideal protein standards are identical to their endogenous counterparts. Expression of recombinant proteins in human cell-free extract systems aids in proper protein folding and post-translational modifications by, e.g., one or more of a protease, kinase, phosphatase, methyl transferase, methylase, acetyl transferase, or acetylase.

FIGS. 2A-2D show results of isotope-labeled green fluorescent protein (GFP) expression using human IVT extracts using two different methods for heavy isotope-labeling. One method used heavy SILAC-labeled cells to produce a heavy isotope-labeled IVT extract. The other used normal light IVT extracts supplemented with heavy isotope-labeled amino acids. Both methods successfully expressed GFP with stable isotope incorporation >95%.

Figure 2A:
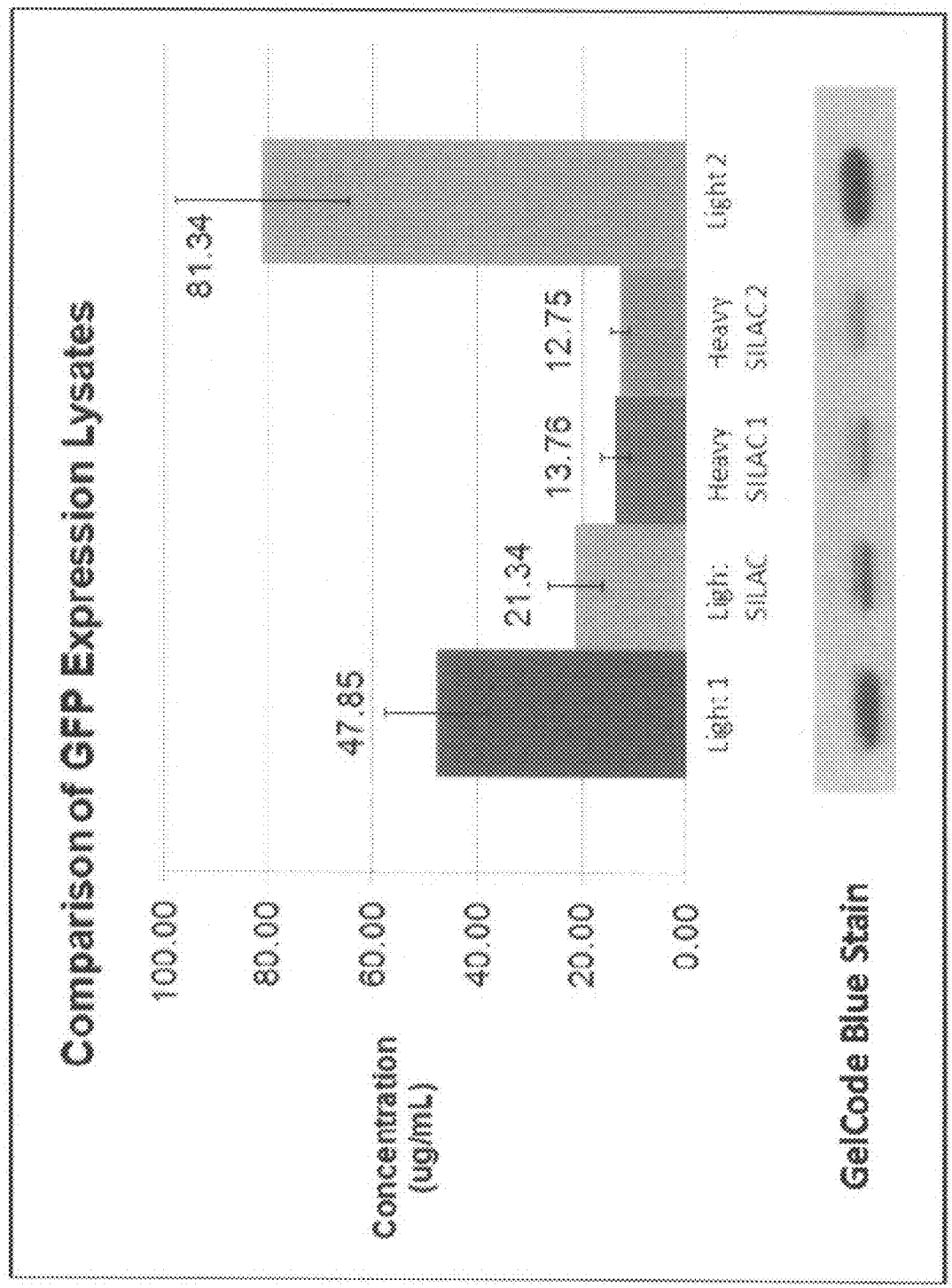
Figure 2C:
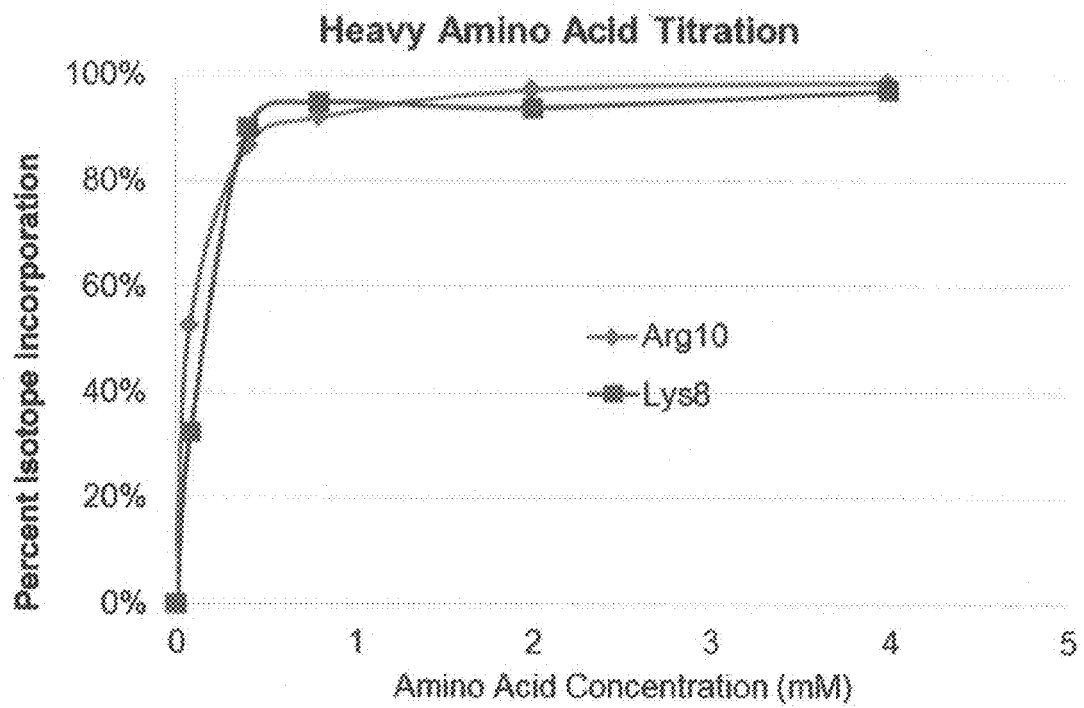
Figure 2D:
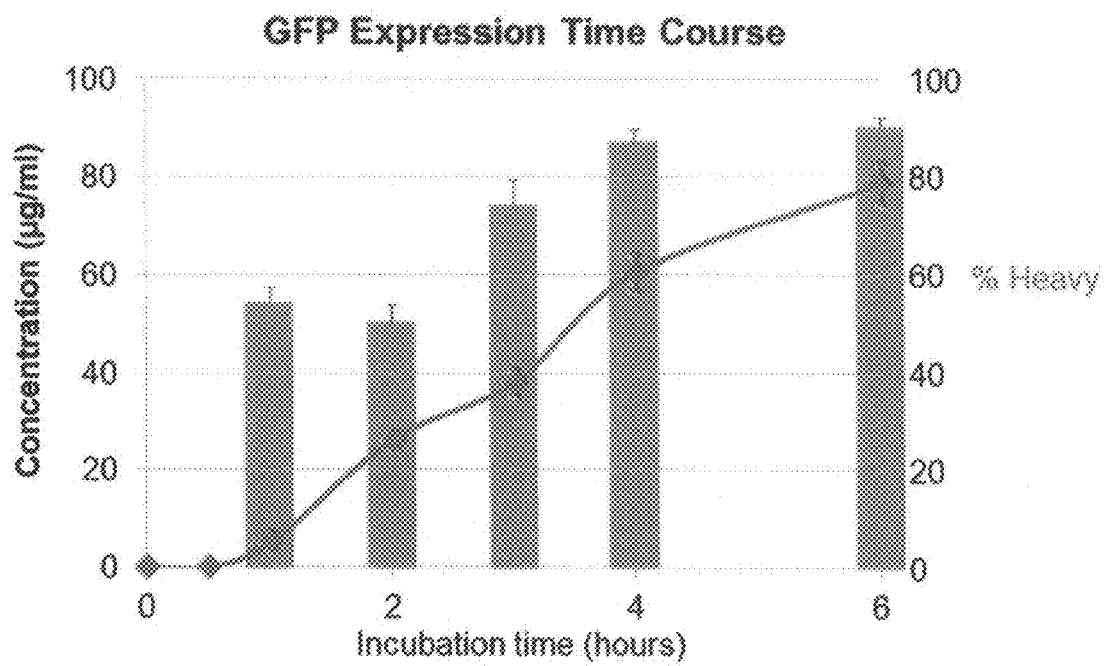

FIG. 2A shows expression of GFP in IVT reactions using HeLa cell lysates derived from cells grown in normal light media that contained normal 10% standard fetal bovine serum; SILAC light media which contained 10% dialyzed fetal bovine serum, 0.1 mg/ml light L-arginine and 0.1 mg/ml L-lysine; or SILAC heavy media that contained 10% dialyzed fetal bovine serum, 0.1 mg/ml $^{13}C_6^{15}N_4$ L-arginine and 0.1 mg/ml $^{13}C_6^{15}N_2$ L-lysine. Protein expression was determined using GFP fluorescence and purified protein staining (GelCode Blue). Light 1 and 2 show typical IVT coupled-protein expression from two different lots of normal lysate. FIG. 2B shows a representative mass spectrum of heavy/light peptide pair used to determine SILAC ratios, i.e., heavy peptide peak area compared to light peptide peak area, and stable-isotope incorporation efficiency. Efficiency was assessed as the percentage of peptide MS signal intensity converted from the light to heavy form. FIG. 2C shows coupled IVT expression of GFP and percent incorporation of stable isotope amino acids in IVT reactions with increasing concentrations of stable isotope-labeled lysine and arginine added to normal, light HeLa protein extracts. FIG. 2D shows coupled IVT expression of GFP and percent incorporation of stable isotope amino acids in GFP with increasing time of incubation using normal, light HeLa protein extracts supplemented with heavy isotope-labeled amino acids.

The light lysates had a significantly higher level of protein expression and lower cost of production (FIG. 2A). Titration and time course experiments using the light lysate with heavy amino acids showed that amino acid concentrations ≥1 mM and incubation times longer than four hours were necessary for optimal protein expression and isotope incorporation (FIGS. 2C, 2D).

Figure 3A:
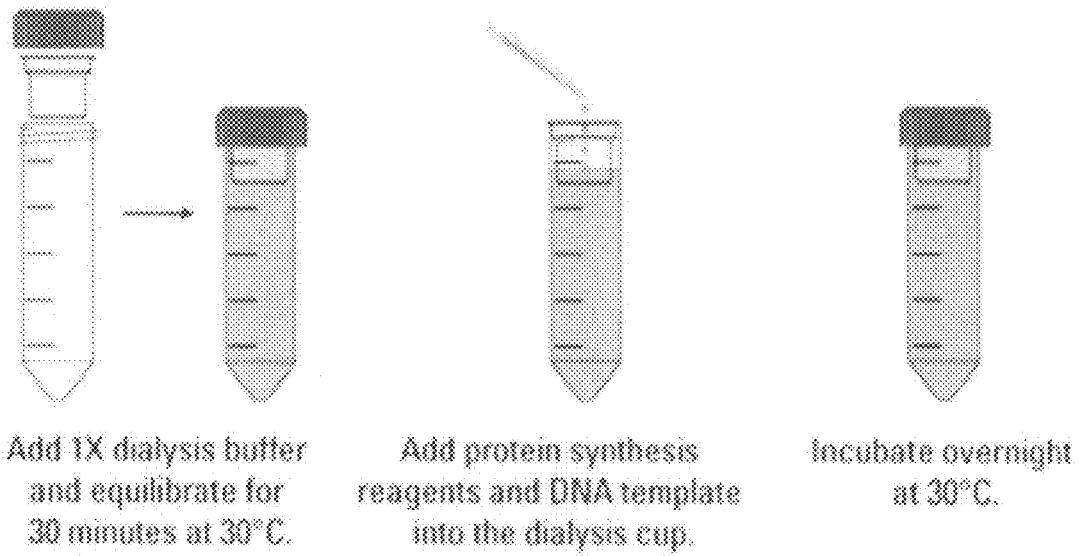
FIGS. 3A-3B schematically show a high-yield human coupled in vitro transcription/translation expression of isotopically-labeled GFP.
Figure 3B:
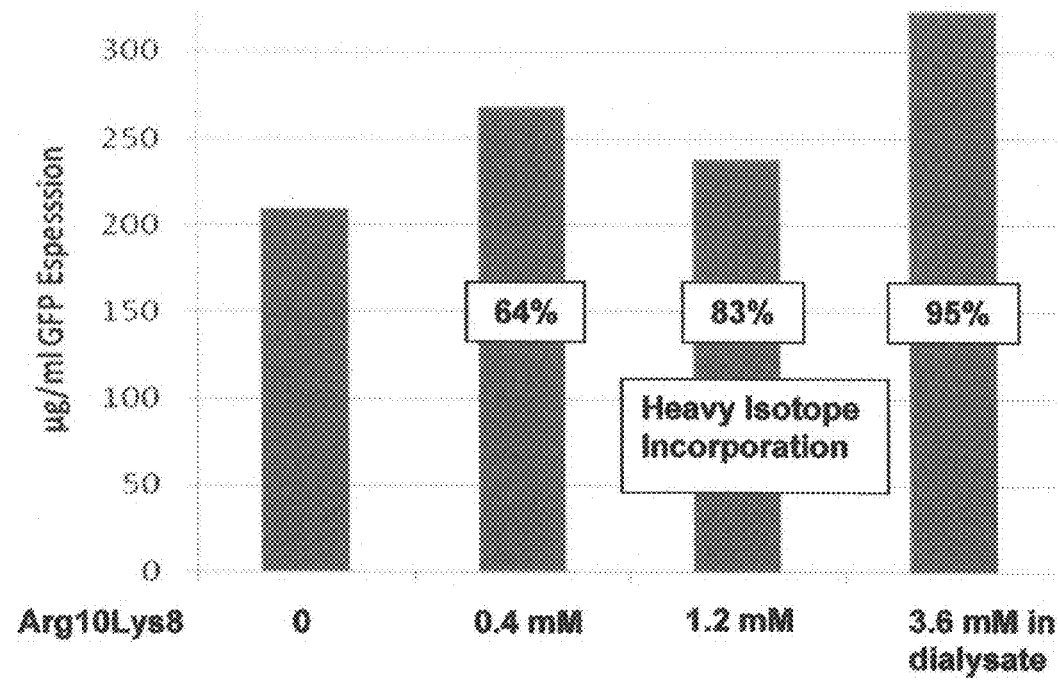

FIGS. 3A-3B schematically show a high-yield human coupled in vitro transcription/translation expression of isotopically-labeled GFP. This high yield embodiment uses a dialysis chamber containing supplemental isotopically labeled amino acids to express heavy isotope-labeled proteins. (FIG. 3A). GFP expression and stable isotope incorporation efficiency are shown in FIG. 3B. The high-yield human IVT extracts were supplemented with 0, 0.4 mM, 1.2 mM and 3.6 mM heavy isotope-labeled amino acids in the dialysate. Heavy labeled-isotope incorporation was 64% with IVT extracts that were supplemented with 0.4 mM heavy-isotope-labeled amino acids. Heavy labeled-isotope incorporation was 83% with IVT extracts that were supplemented with 1.2 mM heavy-isotope-labeled amino acids. Heavy labeled-isotope incorporation was 95% with IVT extracts that were supplemented with 3.6 mM heavy-isotope-labeled amino acids.

To demonstrate the use of stable isotope-labeled GFP as a MS quantitation standard, purified heavy protein was spiked into light GFP samples at different dilutions. FIG. 4 shows linearity of MS quantification using a heavy isotope-labeled protein standard, i.e., stable isotopically-labeled GFP as a standard for MS quantitation of a non-heavy-isotope labeled or light GFP standard dilution. A titration curve of purified heavy isotope-labeled GFP and light GFP, using a fixed amount of stable isotope-labeled GFP (10 fmol), was mixed with unlabeled GFP in ratios from 27:1 to 1:27. Experimental values were fitted to a linear regression line using theoretical expected values. There was a high correlation coefficient ($R^2 > 0.98$) for both arginine and lysine containing peptides over a broad range of peptide concentration ratios.

Figures 5A, 5B:
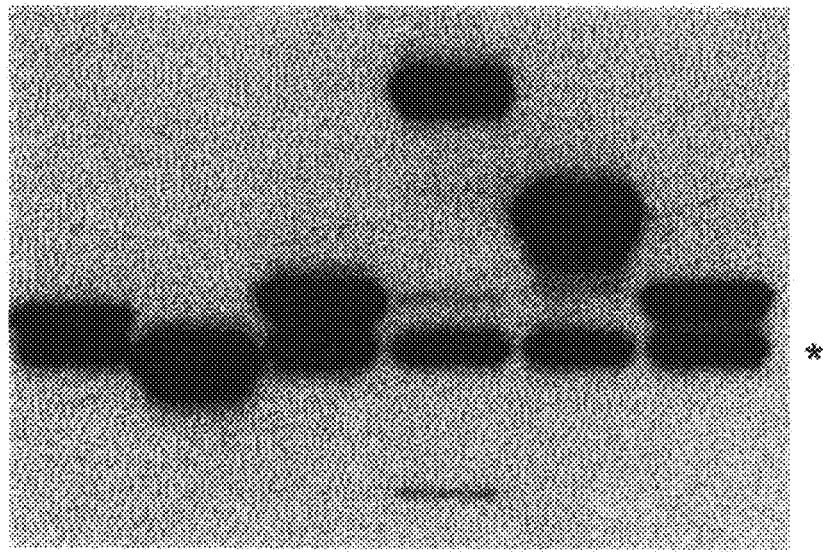

Six additional recombinant proteins were expressed and purified using HA-tag affinity purification to further demonstrate the inventive method for production of human-based proteins. The results are shown in FIGS. 5A-D. FIGS. 5A and 5B show Western blot results of stable isotope incorporation in six different proteins, GFP, BAD, CyclinD1, p53, RB, and GAPDH, expressed using human IVT extracts that were supplemented with heavy amino acids. In FIG. 5A, * indicates an anti-GST cross-reacting band in the lysate. FIG. 5C is a representative MS spectrum of a heavy labeled GAPDH peptide. FIG. 5D is a representative MS spectrum of a heavy labeled cyclin D1 peptide.

Although all proteins were expressed, as indicated by a Western blot, only four out of the six proteins were recovered after purification and sample preparation. Of the proteins identified by MS, all had stable isotope percent incorporations near or exceeding 95%. These results substantiated the applicability of the disclosed IVT system to create heavy protein standards for MS quantitation.

Figure 6A:
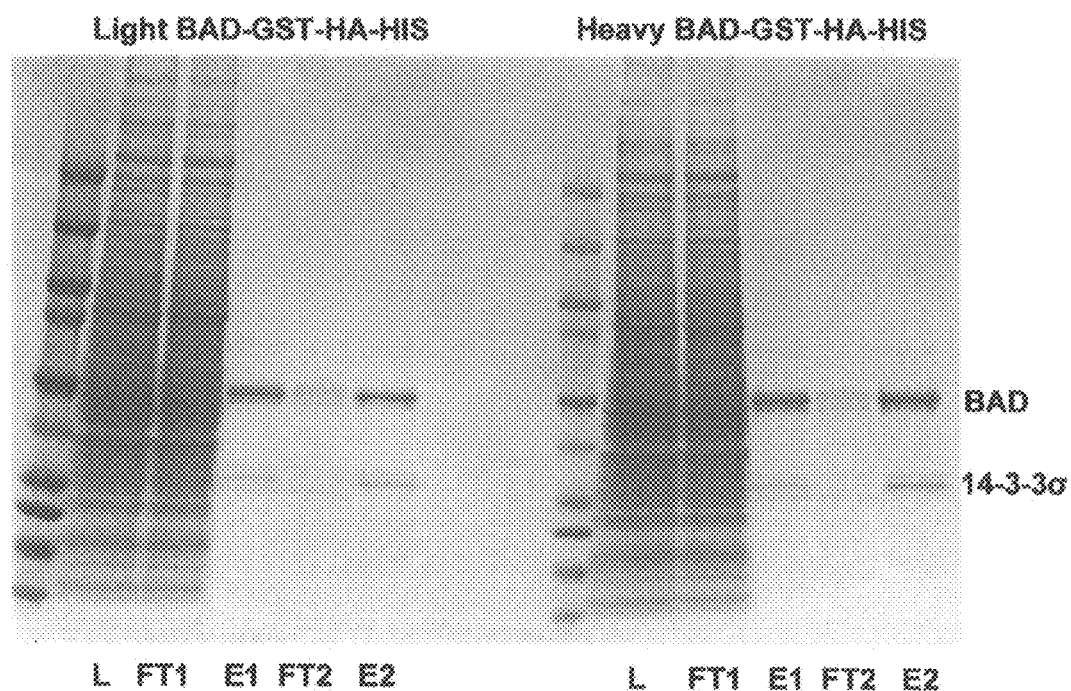

FIGS. 6A-B show expression of a heavy isotope BAD protein and MS analysis. FIG. 6A shows a Coomassie-stained SDS-PAGE gel of recombinant light (left side) and heavy isotope-labeled (right side) BAD-GST-HA-6×HIS purified from HeLa IVT lysates (L), using glutathione resin (E1) and cobalt resin (E2) tandem affinity, with flow throughs (FT) from each column indicated. Sequence coverage and representative MS spectra of stable-isotope-labeled BAD are shown in FIG. 6B; there was >95% isotope incorporated.

The inventive method and system will be further appreciated in view of the following non-limiting examples.

EXAMPLE 1

Heavy Protein Production Using a Human IVT System Derived from SILAC-Labeled Cells A SILAC-labeled HeLa cell lysate was used because this lysate had the highest probability of producing an isotopically-labeled protein. The endogenous amino acids L-lysine or L-arginine and tRNAs linked to these amino acids would be isotopically labeled after 4-5 cell doublings of cells grown in media containing only $^{13}C_6^{15}N_2$ L-lysine-2HCl and/or $^{13}C_6^{15}N_4$ L-arginine-HCl. All proteins in the HeLa cells were >98% labeled using SILAC, determined by MS analysis of lysate protein tryptic peptides. A lysate was prepared using a standard method to produce a cell-free extract amenable to coupled-IVT which is capable for both transcription and translation in a single extract. Test expression of a model protein HIS-tagged GFP from vector DNA confirmed that the heavy lysate was capable of protein expression; protein expression yields were about five-fold less than control unlabeled lysates grown in normal media. This result was reproducible and appeared to be a consequence of poorer cell health before lysate production, possibly linked to the use of dialyzed FBS required for the SILAC method. Despite the low yield of HIS-GFP expression using heavy lysates, the average isotope incorporation for GFP protein based on MS of tryptic peptides was >95% when protein was expressed using extracts supplemented with additional heavy amino acids and exogenous tRNAs were omitted.

This demonstrated production of a heavy protein using a mammalian IVT system. The cost of this method was high and somewhat wasteful because the entire lysate was heavy labeled when only labeling of the expressed protein was required for production of a protein standard. In both control experiments using heavy lysates derived from SILAC cells supplemented with light amino acids, and normal light lysates supplemented with heavy amino acids in reaction mixtures, there was about 30-40% isotope incorporation for both controls after MS analysis of HIS-GFP. Omission of exogenous tRNAs increased isotope incorporation by an additional 10%, to a final average incorporation of 50%. These high levels of incorporation were not expected because traditional eukaryotic IVT systems, e.g., wheat germ or rabbit reticulocyte, typically have <5% isotopically-labeled amino acid incorporation unless they are modified.

EXAMPLE 2

Heavy Protein Production Using a Human IVT System Supplemented with Heavy Amino Acids An efficient and effective way to produce isotopically-labeled proteins was to add heavy amino acids into normal light IVT reaction mixtures. The amount of heavy amino acids, $^{13}C_6{}^{15}N_2$ L-lysine-2HCl and/or $^{13}C_6{}^{15}N_4$ L-arginine-HCl, added to light lysates were titrated from 0 mM, 2 mM, 5 mM, 10 mM, 50 mM, or 100 mM, keeping the remaining amino acid concentrations constant at 2 mM. The isotope incorporation efficiency of expressed HIS-GFP was >95% at heavy amino acid at concentrations >50 mM. In this system, adding exogenous tRNA did not result in decreased isotope incorporation. These results were not expected because the concentration of the amino acid supplement was 2 mM for all amino acids and was believed not to be limiting, i.e., was in excess, for production of proteins in the coupled-IVT system. The amino acid titration experiment was repeated with another protein, HA-tagged BAD, with the same results as for HIS-GFP.

Using the disclosed methods, additional proteins RB, cyclin D1, p53, and GAPDH were expressed and isotope incorporation efficiencies were >95%, as shown in FIG. 5. Heavy protein expression levels observed with traditional methods were about 20% higher than traditional light coupled lysates and were about 4-5 times higher than using a SILAC-labeled lysate. A HIS-GFP expression time course indicated that the inventive heavy amino acid supplement mix may be the source of the higher expression. Different light amino acid concentration mixtures without lysine and arginine provide maximal expression and stable isotope incorporation for heavy amino acids The disclosed method of heavy protein production was significantly less expensive than using a heavy labeled lysate.

During purification of over-expressed heavy HA-BAD, two additional proteins co-purified. Using MS, these proteins were determined to be 14-3-3 proteins that are known to form a heterodimeric complex with phosphorylated BAD. There are numerous sites of modification for phosphorylated BAD peptides, including sites known to be required for 14-3-3 binding. Thus, the function of the proteins expressed using the disclosed heavy IVT system were established; the heavy proteins are being modified and integrated into protein complexes, evidencing both post-translational modification (phosphorylation) and proper folding.

The method is used for both coupled IVT and linked IVT, starting with either DNA or mRNA. The method, in one embodiment, used a dialysis membrane chamber to create an IVT reaction vessel, which was surrounded by a large volume of reaction mixture components that were limited (include amino acids, "energy" mix, and nucleotides). This allowed higher expression of proteins without diluting the lysates, which could limit expression. The expressed heavy proteins are used as a "spike" in standards to measure changes in endogenous proteins by relative MS quantitation.

Five different stable isotope-labeled proteins were produced using a modified non-SILAC human IVT system. The isotope incorporation efficiency was >95% for IVT reactions containing stable-isotope amino acids at concentrations ≥50 mM and incubated for longer than four hours. Spike-in experiments using heavy-labeled protein standards demonstrated MS relative protein quantification linearity.

EXAMPLE 3

Heavy Isotope-Labeled Protein as an Internal Standard for Immunocapture Efficiency or Depletion Specificity Efficiency of immune capture of proteins depends upon the affinity, epitope structure, associated factors, specificity, background, competitors, and other environmental factors (e.g. salts, lipids, etc.). Using the disclosed methods, a stable isotope-labeled full length parathyroid hormone (PTH, 1-115 AA) was expressed and characterized as a C-terminal 6×HIS fusion protein to quantitatively assess sample preparation steps for MS immunoassays. Light and heavy versions of PTH were expressed at high levels (>50 µg/mL) and were highly purified using a cobalt immobilized metal affinity column (IMAC). Heavy PTH isotope incorporation efficiency was assessed using high resolution mass spectrometry and measured to be 96.2% heavy protein labeled based on the average of identified PTH peptides. Light and heavy PTH were combined to demonstrate linearity of quantitation. Heavy PTH was spiked into a human plasma sample containing endogenous processed PTH and the endogenous and heavy PTH were successfully captured using anti-PTH immune capture columns and analyzed using a previously described targeted SRM assay (Lopez et al. (2010) Selected reaction monitoring-mass spectrometric immunoassay responsive to parathyroid hormone and related variants. Clin Chem. 56(2):281-90). In this example, the spiked heavy PTH was used to assess PTH capture efficiency and to normalize results for capture efficiency across multiple samples. In a related example, abundant proteins, including albumin and immunoglobulins, are removed from serum or plasma before or after addition of the heavy isotope-labeled protein standard as an internal standard for depletion specificity.

EXAMPLE 4

Heavy Protein as an Internal Standard for In Vivo Protein Processing and Sample Preparation Digestion Efficiency Mass spectrometric analysis of proteins is typically performed after enzymatic digestion or chemical cleavage of the protein into its constituent peptides. Proteins may also be proteolytically processed in their native environment, and these protein variants may be physiologically relevant and/or have diagnostic utility. For example, assays for monitoring PTH and PTH variants are important for the accurate diagnosis of endocrine and osteological diseases. The heterogeneity of PTH has traditionally been an impediment to developing assays that distinguish full-length PTH (PTH1-84) from N-terminally truncated PTH (PTH 7-84 and others). Because intact and truncated forms of PTH vary in biological activity, assays that can accurately quantify the ratio of intact hormone to its fragments are needed to accurately determine the amount of biologically active PTH. To date, most immunoassays used to monitor PTH levels are based on traditional sandwich ELISA methods that cannot accurately discriminate intact PTH from truncated PTH. These methods typically employ primary antibodies to the N-terminus of the hormone, thereby preventing quantification of any fragments.

Using the disclosed methods, a stable isotope-labeled full length PTH (1-115 AA) was expressed and characterized as a C-terminal 6×HIS fusion protein for use as an internal standard for assessing and quantifying in vivo proteolytic processing of PTH in serum or plasma. After depletion of abundant proteins and/or immune capture of the endogenous and heavy PTH, samples were spiked with unique heavy isoforms of several PTH peptides and enzymatically digested with trypsin. To monitor the numerous isoforms of PTH, PTH and PTH variants were quantified using selected reaction monitoring (SRM) of the depleted and/or immune-enriched samples, using the spiked heavy peptides as quantitative standards. The yield of peptides from heavy PTH digestion is used to assess digestion efficiency and to normalize digestion efficiency across multiple samples.

EXAMPLE 5

Heavy Protein Production for NMR Structural Analysis

Methods to make isotope-labeled protein for NMR application are disclosed. NMR typically required 0.1 mg-1 mg of protein, with all carbons and/or nitrogens isotopically labeled for structural analysis. This requires supplementing the lysate with all amino acids as heavy-isotope labeled amino acids. For this, human cell-free extractions are derived from cells grown using heavy carbon or nitrogen-containing media. IVT extracts are supplemented with reaction components using a mix of amino acids and/or charged tRNAs with all amino acids labeled with $^{15}$N or $^{13}$C. Alternatively, proteins are expressed using normal light human cell-free extracts supplemented with heavy amino acids. In either method, protein isotope incorporation efficiency is verified by MS before NMR analysis. Heavy proteins need to be properly folded and purified for NMR analysis.

All references are specifically incorporated by reference herein in their entirety.

Applicants incorporate by reference the material contained in the accompanying computer readable Sequence Listing identified as Sequence_Listing_ST25.txt, having a file creation date of Jul. 25, 2012 4:22 P.M. and file size of 2.86 KB.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

What is claimed is:

1. An in vitro method for producing heavy isotope-labeled protein, the method comprising
combining a mammalian cell-free extract with at least one mRNA, at least one accessory expression protein, an ATP regeneration system, and a plurality of heavy isotope-labeled amino acids to form an in vitro translation system without supplementing with exogenous tRNA and without supplementing with light amino acids, and
incubating the in vitro translation system under conditions to result in production of at least one heavy isotope-labeled functional protein from the at least one mRNA.

2. An in vitro method for producing heavy isotope-labeled protein, the method comprising
combining a mammalian cell-free extract with at least one DNA, at least one RNA polymerase, at least one accessory expression protein, an ATP regeneration system, and a plurality of heavy isotope-labeled amino acids and/or heavy isotope-labeled tRNAs to form an in vitro transcription/translation system without supplementing with exogenous tRNA and without supplementing with light amino acids, and
incubating the in vitro transcription/translation system under conditions to result in production of at least one heavy isotope-labeled functional protein from the at least one DNA.

3. The method of claim 2 where the mammalian cell-free extract, the at least one accessory protein, and the plurality of heavy isotope-labeled amino acids and/or heavy isotope-labeled tRNAs are preincubated for at least 1 minute prior to combining, without removing any component, the at least one DNA, the RNA polymerase, and the ATP regeneration system.

4. An in vitro method for producing heavy isotope-labeled protein, the method comprising
combining a mammalian cell-free extract with at least one DNA, at least one RNA polymerase, an ATP regeneration system, and a plurality of non-heavy isotope-labeled amino acids and/or non-heavy isotope-labeled tRNAs, thereafter adding a plurality of corresponding heavy isotope-labeled amino acids and/or heavy isotope-labeled tRNAs in a concentration sufficient to replace the non-heavy isotope-labeled amino acids and/or non-heavy isotope labeled tRNAs to form an in vitro transcription/translation system, and incubating the in vitro transcription/translation system under conditions to result in production of at least one heavy isotope-labeled functional protein from the at least one DNA.

5. The method of claim 3 resulting in >50% heavy isotope-labeled incorporation efficiency.

6. The method of claim 1 or claim 2 resulting in a mammalian protein containing at least one post-translational modification.

7. The method of claim 1 or claim 2 where the accessory proteins are selected from the group consisting of $P58^{IPK}$, BiP, eIF2, eIF2B, eIF4E, p97, K3L, E3L, $\gamma_1 34.5$, GADD34, CReP, PP1 regulatory subunit, Nck-1, IMPACT, eIF2B, and combinations thereof.

8. The method of claim 1 or claim 2 where the mammalian cell-free extract is prepared from cultured cells.

9. The method of claim 1 or claim 2 where the mammalian cell-free extract is prepared from human-derived cultured cells.

10. The method of claim 1 or claim 2 where the mammalian cell-free extract is prepared from cells cultured in media containing heavy isotope-labeled amino acids.

11. The method of claim 1 or claim 2 where the heavy isotope is an isotope different in abundance than a naturally occurring isotope.

12. The method of claim 1 where a final concentration of the heavy isotope-labeled amino acid in the in vitro translation system is between 0.05 mM and 0.5 mM.

13. The method of claim 1 or claim 2 where the incorporation efficiency of the heavy isotope-labeled amino acid is 10% to 100%.

14. The method of claim 1 or claim 2 where the heavy isotope is a stable isotope selected from the group consisting of $^{74}Se$, $^{76}Se$, $^{77}Se$, $^{78}Se$, $^{82}Se$, $^{15}N$, $^{13}C$, $^{18}O$, and $^2H$.

15. The method of claim 2 where the incubation is in a dialysis chamber containing external dialysate and internal dialysate, and the method results in relatively higher yield of the at least one heavy isotope-labeled protein from the at least one DNA, compared to incubation not in a dialysis chamber.

16. The method of claim 15 further comprising adding heavy isotope-labeled amino acids to the external dialysate, and supplementing the external dialysate with additional non-heavy isotope-labeled amino acids.

17. The method of claim 1 or claim 2 further comprising using the heavy isotope-labeled protein as a standard for quantitative mass spectrometry; for nuclear magnetic resonance structural analysis; to assess relative recovery of a corresponding native and heavy protein during at least one of lysis, fractionation, enrichment, purification, or immunoprecipitation; to assess relative digestion efficiency of a native protein and the heavy protein; and/or to assess relative post translational modification of a native protein and the heavy protein by at least one post translational protein modification enzyme.

18. The method of claim 1 or claim 2 further comprising purifying the heavy-isotope labeled protein, and quantitating the heavy isotope-labeled protein before or after purification by a method selected from the group consisting of using a fluorescent protein tag as part of the expressed protein sequence, by mass spectroscopy using at least one reference peptide from the protein or from a protein tag, by an enzyme linked immunosorbent assay, Western blot, or antibody-based quantitative assay, by a protein assay method, and combinations thereof.

19. A kit for producing heavy isotope-labeled proteins, the kit comprising a mammalian cell-free extract, a plurality of accessory expression proteins, an ATP regeneration system, a plurality of heavy isotope-labeled amino acids, and instructions for using the kit to form an in vitro translation system according to claim 1.

20. A kit for producing heavy isotope-labeled proteins, the kit comprising a mammalian cell-free extract, an RNA polymerase, a plurality of accessory expression proteins, an ATP regeneration system, a plurality of heavy isotope-labeled amino acids, and instructions for using the kit to form an in vitro transcription/translation system according to claim 2.

21. A kit for producing heavy isotope-labeled proteins in a dialysis chamber, the kit comprising a mammalian cell-free extract, an RNA polymerase, a plurality of accessory expression proteins, an ATP regeneration system, a plurality of heavy isotope-labeled amino acids, and instructions for using the kit to form an in vitro transcription/translation system in a dialysis chamber according to claim 15.

* * * * *